(12) United States Patent
Contos et al.

(10) Patent No.: US 7,413,643 B2
(45) Date of Patent: Aug. 19, 2008

(54) TREATING AN ELECTROCOAT SYSTEM WITH A BIOSURFACTANT

(75) Inventors: Michael A. Contos, Bettendorf, IA (US); Michael J. Bourdeau, Prior Lake, MN (US); Lonnie L. Pillar, Forest Lake, MN (US)

(73) Assignee: Volsper Sourcing, Inc., Minneapolis, MN (US)

( * ) Notice: Subject to any disclaimer, the term of this patent is extended or adjusted under 35 U.S.C. 154(b) by 957 days.

(21) Appl. No.: 10/793,353

(22) Filed: Mar. 4, 2004

(65) Prior Publication Data

US 2004/0231982 A1 Nov. 25, 2004

Related U.S. Application Data

(60) Provisional application No. 60/452,131, filed on Mar. 4, 2003.

(51) Int. Cl.
C25D 13/10 (2006.01)
(52) U.S. Cl. .................. 204/489; 204/509; 204/510
(58) Field of Classification Search ................. 204/489, 204/509, 510
See application file for complete search history.

(56) References Cited

U.S. PATENT DOCUMENTS

| | | | |
|---|---|---|---|
| 4,185,970 A | 1/1980 | Dean | |
| 4,744,950 A | 5/1988 | Hollander | |
| 4,827,959 A | 5/1989 | Muccitelli | |
| 4,995,987 A | 2/1991 | Whitekettle et al. | |
| 5,059,492 A | 10/1991 | Shindou et al. | |
| 5,234,958 A | 8/1993 | Donofrio et al. | |
| 5,278,188 A | 1/1994 | Whitekettle et al. | |
| 5,352,706 A | 10/1994 | Donofrio et al. | |
| 5,403,479 A | 4/1995 | Smith et al. | |
| 5,416,109 A | 5/1995 | Donofrio et al. | |
| 5,416,122 A | 5/1995 | Donofrio et al. | |
| 5,430,078 A | 7/1995 | Hoppe-Hoeffler et al. | |
| 5,512,186 A | 4/1996 | Wright et al. | |
| 5,603,941 A | 2/1997 | Farina et al. | |
| 5,611,939 A | 3/1997 | Hernandez-Mena et al. | |
| 5,624,810 A | 4/1997 | Miller et al. | |
| 5,695,652 A | 12/1997 | Hernandez-Mena et al. | |
| 5,736,056 A | 4/1998 | Wright et al. | |
| 5,763,482 A | 6/1998 | Paterson et al. | |
| 5,891,702 A | 4/1999 | Sakakibara et al. | |
| 5,942,219 A | 8/1999 | Hendriks | |
| 5,997,812 A | 12/1999 | Burnham et al. | |
| 6,017,431 A | 1/2000 | Augustini et al. | |
| 6,066,479 A | 5/2000 | Wright | |
| 6,241,898 B1 | 6/2001 | Wright et al. | |
| 6,290,830 B1 | 9/2001 | Kaylo et al. | |
| 6,350,358 B1 | 2/2002 | Ehmann et al. | |
| 6,757,521 B1 | 6/2004 | Ying | |
| 6,872,291 B2 | 3/2005 | Boyd et al. | |
| 6,977,012 B2 | 12/2005 | Nobutoh et al. | |
| 6,977,013 B2 | 12/2005 | Schroeder et al. | |
| 2001/0008649 A1 | 7/2001 | Layrolle et al. | |
| 2003/0000837 A1 | 1/2003 | Kaylo et al. | |
| 2003/0177978 A1 | 9/2003 | Nobutoh et al. | |
| 2003/0204560 A1 | 10/2003 | Chen et al. | |

FOREIGN PATENT DOCUMENTS

| | | |
|---|---|---|
| CA | 2267678 | 4/1998 |
| CA | 2384195 | 4/2001 |
| CA | 2452014 | 1/2003 |
| DE | 19955372 | 5/2001 |
| EP | 1 239 061 | 9/2002 |
| WO | 99/03933 | 1/1999 |
| WO | WO 00/59834 | 10/2000 |
| WO | WO 01/62084 | 8/2001 |
| WO | WO 01/62091 | 8/2001 |
| WO | 03/004733 | 1/2003 |

OTHER PUBLICATIONS

"Cell Analysis in Real-Time," PCI Paint & Coatings Industry, Biocides Equipment, 2003, 19(7):60-62.

Czechowski, "ATP Technology, A Tool for Monitoring Microbes in Cooling Systems," *American Power Conference*, Chicago, IL, Apr. 10, 1996, 5 pages.

"Toxicant Evaluation Bioscan® ATP Method," MB012 0104, MB Procedures, 2001, BetzDearborn—A Division of Hercules Incorporated, 2 pages.

"Analysis of Biofilm Organisms Bioscan® ATP Method" MB013 014, MB Procedures, 2001, BetzDearborn—A Division of Hercules Incorporate, 4 pages.

"Monitoring of Microbes in Cooling Water Bioscan® ATP Method," MB014, MB Procedures, 2001, BetzDearborn—A Division of Hercules Incorporated, 3 pages.

"Bioscan™ 2 Luminometer Instruction Manual Code L6605," BetzDearborn—A Division of Hercules Incorporated, 12 pages.

(Continued)

*Primary Examiner*—Kishor Mayekar
(74) *Attorney, Agent, or Firm*—Shumaker & Sieffert, P.A.

(57) ABSTRACT

A method of treating an electrocoating process by exposing at least a portion of the process to a biosurfactant admixed in a solution. Methods of treating a surface of an apparatus within an electrocoating operation using a biosurfactant to remove or prevent sessile microorganism growth on the apparatus are provided.

18 Claims, No Drawings

OTHER PUBLICATIONS

"Standard Test Methods for Nonvolatile and Pigment Content of Electrocoat Baths," Destignation: 5145-90 (Reapproved 1997), American Society for Testing and Materials (ASTM) pp. 581-582.

"Bioscan Sampling Pens," Product Instruction Street, BetzDearborn, no date available.

Lee and Deininger, "Rapid Quantification of Viable Bacteria in Water Using an ATP Assay," *American Laboratory News*, 2001, http://www.iscpubs.com/articles/aln/n01101ee.pdf, pp. 24-26.

"Enliten® ATP Assay System Bioluminescence Detection Kit for ATP," Technical Bulletin No. 267, Instructions for Use of Product FF2000, 2002, http://www.promega.com//tbs/tb267/tb267.pdf, Promega Corporation, 5 pages.

"Profile® 1 Rapid Bacteria Detection in Under 5 Minutes," http://www.nhdiag.com/profile_one.shtml, New Horizons Diagnostics Inc., 3 pages, printed Jan. 15, 2003.

"Bioscan™ 2 Microbiological Monitor," Product Fact Sheet, http://www.betzdearborn.com/ind_app_prod/product_family_links. asp?PFL-ID=FS&Pro . . . , BetzDearbon—A Division of Hercules Incorporated, 2 pages, printed Feb. 26, 2002.

"Spectrus™ NX and Bioscan™ ATP Monitoring Dramatically Decrease Bulk Water Counts and Reduce Unscheduled Downtime at Steel Mill," Press Room: Customer Successes, http://www.betzdearborn.com/customer_successes/customersuccesses/asp?CS_ID=1107, Betzdearborn—A Division of Hercules Incorporated, 2 pages, printed Feb. 26, 2002.

"N-Con Systems Bioscan On-Line Toxicity or Treatment Inhibition Monitor Detect Inhibition Before it Becomes Toxicity!" http://www.n-con.com/bioscan.html, N-Con Systems Co., Crawford, GA, 5 pages, printed Oct. 12, 2004.

Wooten, "An Inhibition Monitor for Rapid Wastewater Screening," Water Environment Federation and Purdue University Industrial Wastes Technical Conference, 2000, St. Louis, MO, 10 pages.

Walker, "New Microbiological Monitoring Methods for Water Systems," *Spec. Chem.*, 1993, 13(3): 110-111.

Winkowski, K. et al., "Controlling Microbial Contamination," Jul. 2002, Paint & Coatings Industry, vol. 18, Issue 7, p. 60-66.

Paint and Coatings Industry, "Paint and the Constant Threat of Microbial Attack: Why a Constant Vigil is Needed," Jul. 2000, p. 64-74.

Chu et al., "Using ATP Bioluminescence Technique for Monitoring Microbial Activity in Sludge," Biotechnology and Bioengineering, vol. 75, No. 4, Nov. 20, 2001, pp. 469-474.

International Preliminary Report on Patentability for PCT/US2004/006683, mailed Feb. 3, 2005.

Canadian Official Action dated Oct. 19, 2007, for related Canadian patent application No. 2,517,550, filed Mar. 4, 2004, (6 pages).

PCT Written Opinion for PCT/US04/006684, mailed Feb. 11, 2005.

TREATING AN ELECTROCOAT SYSTEM WITH A BIOSURFACTANT

RELATED APPLICATIONS

This application claims the benefit of priority under 35 U.S.C. § 119(e)(1) of U.S. Provisional Application No. 60/452,131, filed Mar. 4, 2003.

TECHNICAL FIELD

This invention relates to industrial cleaning methods, and more particularly to a method for treating electrocoat systems to remove or inhibit micro-organism growth.

BACKGROUND

Electrocoat finishing systems are typically warm, damp places and undesirably provide conducive conditions for microorganism growth. Once microorganisms colonize on an electrocoat system, removing the contamination is very difficult and can be quite costly. High levels of contamination in the system can lead to increased reject rates for parts or operational issues with the finishing system.

Various techniques have been implemented in the industry to combat microorganism growth in electrocoat tanks and equipment. Power washing and other physical removal methods have been used, for example. Other conventional methods include chemical-based treatments, such as the use of biocides, solvents, halogen-based chemicals (e.g., Cl, Br,), and metal-containing (e.g., Cu, Ag) compounds. Existing methods for cleaning have several drawbacks. Some of the cleaning chemicals are toxic and/or expensive, the treatments tend to be very labor intensive, many of the contaminated areas cannot be accessed easily, and effectiveness cannot readily be gauged until days after the process is complete. Furthermore, regulatory agencies continue to add or revise laws and guidelines relating to the amounts of solvents allowed to be released into air and water waste streams. Thus, practitioners in the electrocoating industry are encouraged to develop more "environmentally friendly" processes. This, however, leads to increased conditions for microorganism growth.

What is needed is a method for removing microorganism growth from electrocoating equipment that can be easily practiced and has minimal negative impact on the environment.

SUMMARY OF THE INVENTION

The invention provides a method for treating electrocoating equipment using a biosurfactant that can be easily practiced. Advantageously, certain methods of the invention can help minimize the amount of defective electro-finished parts that are manufactured when microorganism growth is not controlled. Furthermore, an exemplary method can provide a way to treat an electrocoating operation using environmentally-friendly biosurfactant materials.

Placed in solution and applied to a surface of an apparatus within an electrocoating operation, a biosurfactant can be effective in removing microorganisms that adhere to surfaces of the apparatus. A biosurfactant can also aid in inhibiting free-floating micro-organism from anchoring onto an electrocoating operation and transforming into sessile systems.

In an aspect of the invention, a method of treating an electrocoating operation includes admixing an effective amount of biosurfactant into a solution; and exposing the surface to the admixture of biosurfactant and solution. Where the surface has a population of sessile microorganisms, the biosurfactant can have an available concentration sufficient to breakdown the adherence between at least a portion of the microorganisms and the surface.

In another aspect, microorganism growth in an electrocoating operation can be inhibited by applying a biosurfactant to a surface of an electrocoating apparatus; and admixing an amount of a biocide to a liquid stream within the electrocoating operation.

In a further aspect, an electrocoating operation is provided that includes systems for surface preparation, electrocoat application, post rinsing, and curing; and a microorganism inhibiting system integrated with at least one of those systems.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

The invention provides a method of treating an electrocoating operation to control (e.g., remove, minimize, and/or inhibit) micro-organism growth in the liquid streams and/or the equipment surfaces of the electrocoating operation. When implemented, certain methods can inhibit further growth of a micro-organism population, and possibly prevent future populations from generating within the operation, or anchoring onto a surface of the equipment. Thus, advantageously, certain methods of the invention extend the time between conventional cleanings that can often entail non-environmentally friendly methods.

A preferred method of the invention includes use of a biosurfactant to treat target areas within an electrocoat process. A biosurfactant as used herein, is a material that can penetrate the microorganism layer(s) and dislodge microorganisms (e.g. sessile microorganisms) at their anchor site. Generally, a biosurfactant does not kill microorganisms or colonies when used alone. Biosurfactants have also been referred to in industry as biodispersants or biopenetrators. They are generally non-toxic and environmentally friendly, both characteristics being highly desirable for many practitioners.

Target areas suitable for treatment by a biosurfactant, alone or in solution, include any equipment that is within an electrocoating operation. This would encompass tanks, pipes, conveyors, monorails, sprayers, walls, etc. Of particular interest can be a post-rinse system of an electrocoating process, as the equipment in there tends to have conditions highly conducive to microorganism growth.

Advantageously, a method of the invention can be useful in controlling the generation and growth of micro-organism layers (e.g., biofilm) in hard-to-reach areas within an electrocoating process. Pipes and spray apparatuses (e.g., risers, nozzles), for example, can be highly susceptible to building up biofilm layers. These areas, however, can be treated and cleaned using a method of the invention, since the challenge of 'reachability' can be overcome. For example, an enclosed cavity or a narrow tubular area that is typically unreachable or inaccessible by a hand or tool can be treated by flowing and contacting a biosurfactant to the sessile microorganisms.

A biosurfactant can be particularly effective in areas of the process that are substantially completely immersed such as surfaces of liquid tanks and plumbing. If a target area is not substantially immersed, however, a cleaning technique that implements manual or pressurized cleaning following a biosurfactant treatment may be desirable. As will be discussed further, exposing a surface of an electrocoating apparatus to a biosurfactant can be conducted in a variety of ways, such as by pumping a biosurfactant in solution past the surface, spraying the biosurfactant onto the surface, washing down the surface with a material that can retain the biosurfactant (e.g. towel, sponge, etc), or pressurized washing with water, or combinations thereof. Depending on the type of surface or equipment a practitioner seeks to treat, the delivery method for the biosurfactant for contacting the surface(s) can be adjusted accordingly.

In a method of the invention, a biosurfactant is preferably incorporated into a solution to attack micro-organisms that adhere to a surface. The biosurfactant can be admixed to a solution so that the concentration in the solution is sufficient to break down the adherence between sessile micro-organisms and the surface onto which they adhere. In certain embodiments, the biosurfactant is present in a solution at a concentration of about 5 to about 10,000 ppm, although the range may be broader in instances where the microorganism level is relatively high. Without limitation, a useful range of the concentration for the biosurfactant in a solution is about 10 to about 1000 ppm.

Suitable biosurfactants include compounds compatible with liquid streams generally associated with an electrocoating process. Certain biosurfactants are commercially available and useful for embodiments of the invention, including, for example, Nalco 2890 (Nalco Corp; Naperville, Ill.), FREMONT 9106 (Fremont Industries; Shakopee, Minn.).

The biosurfactant can optionally be provided and used as an admixture of biosurfactant and solvent. Exemplary solvents include, but are not limited to, water, organic acids, amines, solvents, biocides, and combinations thereof. Inclusion of an organic acid can be useful for cathodic electrocoat processes and can be, for example, acetic, lactic, formic, dimethylpropionic (DMPA), propionic acids and combinations thereof. For anodic electrocoat processes, it may be useful to add amines in the biosurfactant solution, such as diisopropanol amine (DIPA), diethylethanol amine (DEEA), dimethylethanol amine (DMEA), triethanol amine (TEA), etc. Suitable solvents for a biosurfactant solution include, for example, glycol ethers (e.g. ARCOSOLVE PnP™; PROPA-SOL™ P—propylene glycol mono propyl ether); CELLO-SOLVE™ compounds (Dow Chemicals; Midland, Mich.) such as butyl CELLOSOLVE™ (ethylene glycol monobutyl ether); and DOWANOL PM™ (Dow Chemicals)—propylene glycol methyl ether). Biocides and other biological agents can include, but are not limited to, bleach, glutaraldehydes (e.g., UCARCIDE 225™) KATHON EDC, and other agents such as those supplied by Troy Chemical Industries, Inc. (e.g., MERGAL™ 174, 186).

Optionally, the biosurfactant can be added to a warmed solution. An admixture of biosurfactant and solution can be at a temperature that enhances the break down of the adherence properties between the microorganisms and their host surface (s). In an aspect, the solution prior to admixture of the biosurfactant can have a temperature of about 75° F. to about 200° F. Alternatively, the admixture of biosurfactant and solution, at about the point of contact with the microorganisms can be used at an elevated average temperature, such as about 70° F. to 200° F. The bio surfactant in solution can also be warmed to about 90° F. to about 120° F. The raised temperature can be achieved by a variety of conventional techniques, including for example, immersion heaters, addition of higher temperature liquid components, and liquid circulation that initiates temperature increases.

Circulation or movement of the biosurfactant alone or in solution can also enhance the breakdown of a biofilm, particularly when manual cleaning or other mechanical forces are not implemented. A biosurfactant solution can be circulated through or past a target site for at least about 24 hours. In certain embodiments, such as during a routine cleaning procedure, sufficient microorganism control can be achieved by circulating for at least about 4 hours. In some embodiments of the method, both applied heating and circulation can be used.

In another aspect of the invention, a method can be implemented whereby an amount of biosurfactant can be added directly into a liquid stream of an electrocoat process while the electrocoating process is in operation. This method can be used as an alternative to intermittent or scheduled treatments where equipment is exposed for a pre-determined period, as in a cleaning or maintenance procedure, or, the method can be practiced as an additional mode for treating an electrocoating operation. Thus, it is within the purview of the invention that an electrocoating operation can implement an ongoing treatment where, for example, one or more liquid streams within an electrocoating operation are pre-loaded with a biosurfactant, where the biosurfactant is present in a concentration throughout the process at a level that inhibits microorganism adherence to surfaces. As an additive to a liquid stream, the biosurfactant can prevent microorganisms from adhering and colonizing on electrocoating equipment, thereby preventing contamination within the process. Liquid streams or liquid supplies of an electrocoat process that can be pre-loaded with biosurfactant to aid in minimizing sessile microorganism layers from developing include for example, paint in supply drums, pipes and tanks, as well as post-rinse water and other liquids. The biosurfactant can be provided in concentrated form prior to addition to a liquid supply or stream. For example, a biosurfactant can be concentrated (in the liquid supply/stream) ten times more than the concentration level at which it exists during a coating operation. In an aspect, the biosurfactant can be provided at about 3 to about 5 times greater concentration than a typical operating concentration level.

In certain processes, it may be advantageous to implement a biosurfactant treatment in combination with other conventional cleaning and preventative techniques, such as pressure washing, use of biocides, and manual scrubbing. Biocides can provide a synergistic effect when used in conjunction with a biosurfactant, as a biocide can destroy and possible eliminate a targeted species of microorganism. The biosurfactant can be circulated through an electrocoat process before a biocide is added to the process. In an exemplary method, a biosurfactant can be applied and used in the electrocoat process equipment about 15 to about 60 minutes before adding a biocide to the process.

To determine the effectiveness of a biosurfactant treatment, it can be advantageous to determine microorganism levels at least before the treatment, and preferably before and after implementing a treatment. Analyzing a sample from a target site (liquid stream or equipment) can also be useful in determining which biocide, if any, can obliterate the microorganism population, or which biosurfactant would be most effective in breaking down the sessile microorganism layers. The analysis can be performed using a variety of methods and devices capable of evaluating levels and presence of microorganisms in a sample. Liquid samples, for example, can be evaluated using a detection device such as those based on ATP technology. A suitable method is described in a U.S. patent application bearing Ser. No. 10/792,937. As described therein, a preferred device is one that can provide rapid and nearly instantaneous evaluation of the level of microorganism in a liquid sample. One such device is available commercially from GEBetzDearborn, under the tradename BIOSCAN.

As just described, a baseline or point of reference as to what microorganisms are present and how much, can be advantageous. Thus, in practice, a method of the invention can include a step of initially analyzing a sample from one or more target areas within the electrocoating process to obtain a baseline reflecting the level of microorganism contamination in the system. Samples from more than one region of the process are preferably obtained for evaluation. When indications exist that microorganism contamination is not widespread throughout the process, contamination sources or 'hot spots' may be evident and therefore can be easily targeted. Immediately following a biosurfactant treatment, a determination of the level of microorganisms left in the system, can advantageously provide an assessment as to whether the treatment or cleaning was effective and/or whether additional treatment would be necessary.

Biofilms can exist on surfaces as thin layers. Therefore in addition to testing liquid samples from an electrocoating operation to determine the effectiveness of a biosurfactant treatment, it is also useful to test equipment surfaces for presence of microorganisms. For example, swabbing surfaces and testing them with a device that can determine the contamination level on the host surface can also be useful in assessing the results of the biosurfactant treatment.

A post rinse stream of an electrocoat system is typically monitored, as the area can often accumulate biofilm layers easily. Treatment of these systems can be performed more often than other areas of the process, and if desired, can be implemented for greater lengths of cleaning time.

Significant decreases in contamination can be achieved in the practice of the invention. Within about 24 hours, a system treated with a biosurfactant according to a method of the invention can have stabilized microorganism levels. However, variations may exist in the effectiveness of the biosurfactant treatment or length of time required to achieve a desired level, depending on how severe the contamination was at the start of the cleaning process. Factors that may also affect the readings (e.g., detected levels) include very heavy contamination and/or the possibility that an added biocide has not peaked in effectiveness.

During analysis and monitoring of a cleaning procedure where only a biosurfactant solution treatment is used (e.g. no additional cleaning factors such as biocides or manual scrubbing, etc.), the system can experience an increase in the microorganism levels (e.g., colony forming units (CFU's)) in the early stage of the procedure. This can be an indication that sessile colonies from the process equipment are being dislodged or removed and therefore could be "free floating" or planktonic. If the detection levels are significantly higher, a practitioner may wish to discard the liquid streams of an electrocoat system, refill it, and add fresh biosurfactant at that time.

For continuous monitoring or to achieve a sufficient understanding of how "clean" the system is progressing, it may be useful to obtain a reading of the microorganism level on an intermittent basis. Preferably, multiple readings throughout the process are taken on a predetermined schedule. When using a biosurfactant cleaning solution alone (i.e. not in conjunction with a biocide), a process can often "peak" at a certain detectable microorganism level. At that point, it may suggest that the majority of the microorganism colonies have been stripped from the various surfaces and plumbing within the electrocoat system.

When using a biosurfactant cleaning solution in combination with a biocide, circulation of the solution through the system can be implemented and continued until the detectable levels are consistently at about 50% or less than the initial detected level prior to the start of circulation. Use of a biocide in conjunction with a biosurfactant can result in a decrease in the amount of microorganisms detected even in the early stages of the procedure. However, the detected levels should be scrutinized, as they can appear inconclusive-as both removal and eradication of microorganisms can be occurring simultaneously.

Optionally, a biosurfactant treatment can be followed by a water rinse. Preferably, deionized water/reverse osmosis treated water (DI/RO) is used for the rinse. To ensure sufficient rinsing, it may be useful to discard the contaminated liquid streams first, wash the containers, and then follow with a second, subsequent rinse with DI/RO water. A thorough cleaning and rinsing sequence can help to insure the electrocoat equipment, particularly the pipes (e.g., plumbing) are free of planktonic (free floating) colonies that may try to re-attach to various surfaces. For processes that have spray nozzles, it may be advantageous to initially remove the spray nozzles prior to rinsing. This is to prevent the nozzles from clogging with any biomass that has been dislodged during the cleaning process. Soaking the nozzles in a bleach solution can be implemented to dissolve and remove biomass from dispensing equipment.

Other steps that can optionally be practiced in certain methods of the invention include: manually cleaning or pressure washing target sites; use of scrub tools; swabbing surfaces and testing samples from those swabs; passage of DI water through a submicron filter (preferably before adding the water to a post rinse system); and testing of all water supplies, particularly that used in a post rinse system.

A method of the invention implemented in an electrocoating operation can result in elimination or decreased levels of microorganisms sustained for at least one week of continuous electrocoat operating time. If relatively heavy contamination reappears and is detected within a short period, such as less than one week, it could be an indication that either a microorganism source had not been identified and addressed, or colonies were missed during treatment. Thus, in certain methods, as mentioned earlier, a treatment with a biosurfactant can benefit from initially identifying the largest populations of microorganisms and subsequently choosing a compatible, effective biosurfactant.

Once a thorough treatment of an electrocoat process has been performed, it can be advantageous at that point to implement a preventive maintenance plan. Repeated, or intermittently scheduled treatments such as in a preventive maintenance schedule, can also be useful, particularly in heavily contaminated areas or areas that are prone to such contamination.

When practicing a method of the invention, it is preferred that the post rinse region of the process is isolated from the electrocoat tank. This can prevent material that is incompatible with electrocoat baths from entering the tank. For example, bleach is a component that can be detrimental to an electrocoating process if it enters an electrocoat tank.

It is within the purview of the invention that a microorganism inhibiting system used to practice the method described herein can be integrated with an electrocoating operation. For example, a process can include, among other things, a surface preparation system followed by an electrocoating application system, a post rinse system following the electrocoating application system, a curing system following the post rinse system; and a microorganism inhibiting system integrated with one or more of the process steps—surface preparation, electrocoat, post rinse, and curing systems. The microorganism inhibiting system can include a dispensing apparatus configured to add an effective amount of a biosurfactant and/or a biocide to a desired portion of the electrocoating system.

As described above, it is contemplated that an electrocoating solution can be provided that includes a biosurfactant dispersed in a solution. The biosurfactant can be present in an amount sufficient to breakdown the adherence between sessile microorganisms and a surface of an apparatus within an electrocoating operation. A solution as described herein can be added directly to any portion of an electrocoating process, any liquid stream that passes through or is maintained in the process, or it be used as a direct cleaning solution.

A number of embodiments of the invention have been described. Nevertheless, it will be understood that various modifications may be made without departing from the spirit and scope of the invention. Accordingly, other embodiments are within the scope of the following claims.

EXAMPLES

Example 1

The following schedule and procedure is an exemplary cleaning method useful in a post-rinse portion of an electrocoating operation.

Day 1

1. Sample and test various liquid streams and surfaces with a detection device to obtain a baseline.

2. Treat the liquid in the electrocoat tank by adding 0.5-1.0% biocide. Biocide can be premixed with permeate and/or post rinse material prior to addition to the main ecoat tank to ensure proper incorporation.

3. Direct remaining post rinse materials to waste treatment in preparation for in-depth cleaning process. Isolate post rinse system from main ecoat tank.

4. Add 0.5% Bleach solution to each post rinse tank/system and circulate overnight (e.g., at least 8-10 hours). Remove end-caps of pipes initially after pumps have started to remove bacteria build up from piping. Replace end-caps and circulate the solution through spray risers. As feasible, utilize a power washer to attack recessed areas of the housing.

Day 2

5. Drain post-rinses of bleach solution, rinse with water, and begin refilling for next step of treatment plan.

6. Remove post rinse nozzles, soak in a highly diluted bleach solution, and replace with new nozzles.

7. Add biosurfactant (with acid and solvent if necessary) and circulate in the post-rinses (e.g., 24-hour circulation period, 100° F. temperature, 500 ppm concentration). Test rinse water every 6 hours with a detection device (readings may go up as sessile bacteria sloughs off surfaces and begins to float in rinse solution).

a. As feasible, power wash and/or manual scrub post-rinses to clean areas not exposed to biosurfactant through spray risers. Swab surfaces that are manually cleaned and verify the cleanliness of the system using the detection device.

Day 3

8. After initial cleaning period, lower all rinse tanks and rinse with additional water to ensure all undesired colonies are removed. Manually inspect all post-rinse walls, plumbing, etc. and swab all surfaces to confirm adequate cleaning.

9. Re-clean any missed areas manually to ensure removal of microorganisms and verify for cleanliness. Drain post rinse and permit post rinse system to dry overnight (e.g., 8-10 hours).

Day 4

10. Refill all post-rinses and begin circulation. Sample water streams after twelve hours of circulation.

11. Redirect permeate to the last post rinse and begin counterflowing. Change all bag filters on system and replace ultra-filter membranes.

What is claimed is:

1. A method of treating an electrocoating apparatus comprising:
 admixing an effective amount of biosurfactant into a solution; and
 exposing at least a portion of the electrocoating apparatus to the admixture of biosurfactant and solution.

2. The method according to claim 1, wherein the electrocoating apparatus comprises an apparatus having a surface, the surface comprising a population of sessile microorganisms; and wherein the biosurfactant is available at a concentration sufficient to break down; the adherence between at least a portion of the sessile microorganism population and the surface.

3. The method according to claim 1, wherein the concentration of the biosurfactant in the admixture is about 5 to about 10000 ppm.

4. The method according to claim 1, wherein the concentration of the biosurfactant in the admixture is about 10 to about 1000 ppm.

5. The method according to claim 1, wherein the solution has a temperature of about 75° F. to about 200° F.

6. The method according to claim 1, wherein the solution has a temperature of about 90° F. to about 125° F.

7. The method according to claim 1, further comprising applying heat to the admixture of biosurfactant and solution.

8. The method according to claim 1, further comprising circulating the admixture of biosurfactant and solution through at least a portion of the electrocoating apparatus.

9. The method according to claim 8, wherein the admixture of biosurfactant and solution, is circulated for at least about 4 hours.

10. The method according to claim 1, further comprising adding a biocide to a liquid stream within the electrocoating apparatus.

11. The method according to claim 1, wherein the solution comprises water.

12. The method according to claim 1, further comprising determining a level of microorganisms present in a liquid stream within the electrocoating apparatus.

13. The method according to claim 1, further comprising identifying the type of microorganisms present in a liquid stream within the electrocoating apparatus.

14. The method according to claim 1, further comprising determining a first level of microorganism present in a liquid stream within the electrocoating apparatus prior to exposing the at least a portion of the apparatus to the admixture of biosurfactant and solution; and determining a second level of microorganism presence in the liquid stream after exposing the at least a portion of the process to the admixture of biosurfactant and solution, wherein the second level is less than the first level.

15. The method according to claim 1, wherein the step of admixing is performed within the electrocoating apparatus.

16. A method of removing microorganisms from an apparatus of an electrocoating process comprising: applying a biosurfactant to a surface of the apparatus.

17. The method according to claim 16, wherein the apparatus is a post-rinse system, and the method further comprises:
    draining a tank of the post-rinse system to expose a surface of the system prior to exposing the surface with the biosurfactant.

18. A method of inhibiting micro-organism growth in an electrocoating operation comprising:
    applying a biosurfactant to a surface of an apparatus within the electrocoating operation; and
    admixing an amount of a biocide to a liquid stream within the electrocoating operation.

* * * * *

UNITED STATES PATENT AND TRADEMARK OFFICE
CERTIFICATE OF CORRECTION

| | | |
|---|---|---|
| PATENT NO. | : 7,413,643 B2 | |
| APPLICATION NO. | : 10/793353 | |
| DATED | : August 19, 2008 | |
| INVENTOR(S) | : Michael A. Contos, Michael J. Bourdeau and Lonnie L. Pillar | |

It is certified that error appears in the above-identified patent and that said Letters Patent is hereby corrected as shown below:

Title page item [73]
The Assignee should read -- Valspar Sourcing, Inc. --

Signed and Sealed this

Eighteenth Day of November, 2008

JON W. DUDAS
*Director of the United States Patent and Trademark Office*